(12) United States Patent
Yang (10) Patent No.: US 7,041,086 B2
(45) Date of Patent: May 9, 2006

(54) SAFETY SYRINGE NEEDLE

(76) Inventor: Chang-Ming Yang, No.27, GuangFu Rd., Junan Ien, Miaoli (TW)

( * ) Notice: Subject to any disclaimer, the term of this patent is extended or adjusted under 35 U.S.C. 154(b) by 33 days.

(21) Appl. No.: 10/316,859

(22) Filed: Dec. 12, 2002

(65) Prior Publication Data
US 2004/0116877 A1 Jun. 17, 2004

(51) Int. Cl.
*A61M 5/32* (2006.01)
(52) U.S. Cl. ................ 604/198; 128/919
(58) Field of Classification Search ........... 604/192, 604/198, 110, 263, 162, 163, 171, 181, 187; 128/919
See application file for complete search history.

(56) References Cited

U.S. PATENT DOCUMENTS

| | | | | |
|---|---|---|---|---|
| 3,134,380 A | * | 5/1964 | Armao | 604/198 |
| 4,775,369 A | * | 10/1988 | Schwartz | 604/263 |
| 4,915,697 A | * | 4/1990 | DuPont | 604/192 |
| 5,290,254 A | * | 3/1994 | Vaillancourt | 604/192 |
| 5,582,597 A | * | 12/1996 | Brimhall et al. | 604/192 |
| 5,667,496 A | * | 9/1997 | Wilson, Jr. | 604/263 |
| 5,700,249 A | * | 12/1997 | Jenkins | 604/263 |
| 5,743,888 A | * | 4/1998 | Wilkes et al. | 604/198 |
| 5,891,099 A | * | 4/1999 | Nakajima et al. | 604/164.08 |

\* cited by examiner

*Primary Examiner*—LoAn H. Thanh (57) ABSTRACT

A safety structure for a needle of a syringe including an external bushing connected with a base, and a barrier structure on the base contacts with the needle, which has an extended bushing on a base frame. At the front end of the bushing there is an extended cannula with an outer edge through which a needle is inserted. The external bushing is made of soft materia. A trocar boring on a front end of the base is connected with the trocar-admitting part. Moving the barrier structure away from the needle and pushing the base back, the trocar boring of the base covers outside of the outer edge of the needle. The base is fixed on the needle by friction between a wall of the trocar boring and the outer edge of the cannula.

4 Claims, 16 Drawing Sheets

SAFETY SYRINGE NEEDLE

BACKGROUND OF THE INVENTION

1. Field of the Invention

This invention is related to a type of syringe needle, especially refers to a syringe needle that incorporates the needle cover with the needle.

2. Description of the Prior Art

Figure 22:
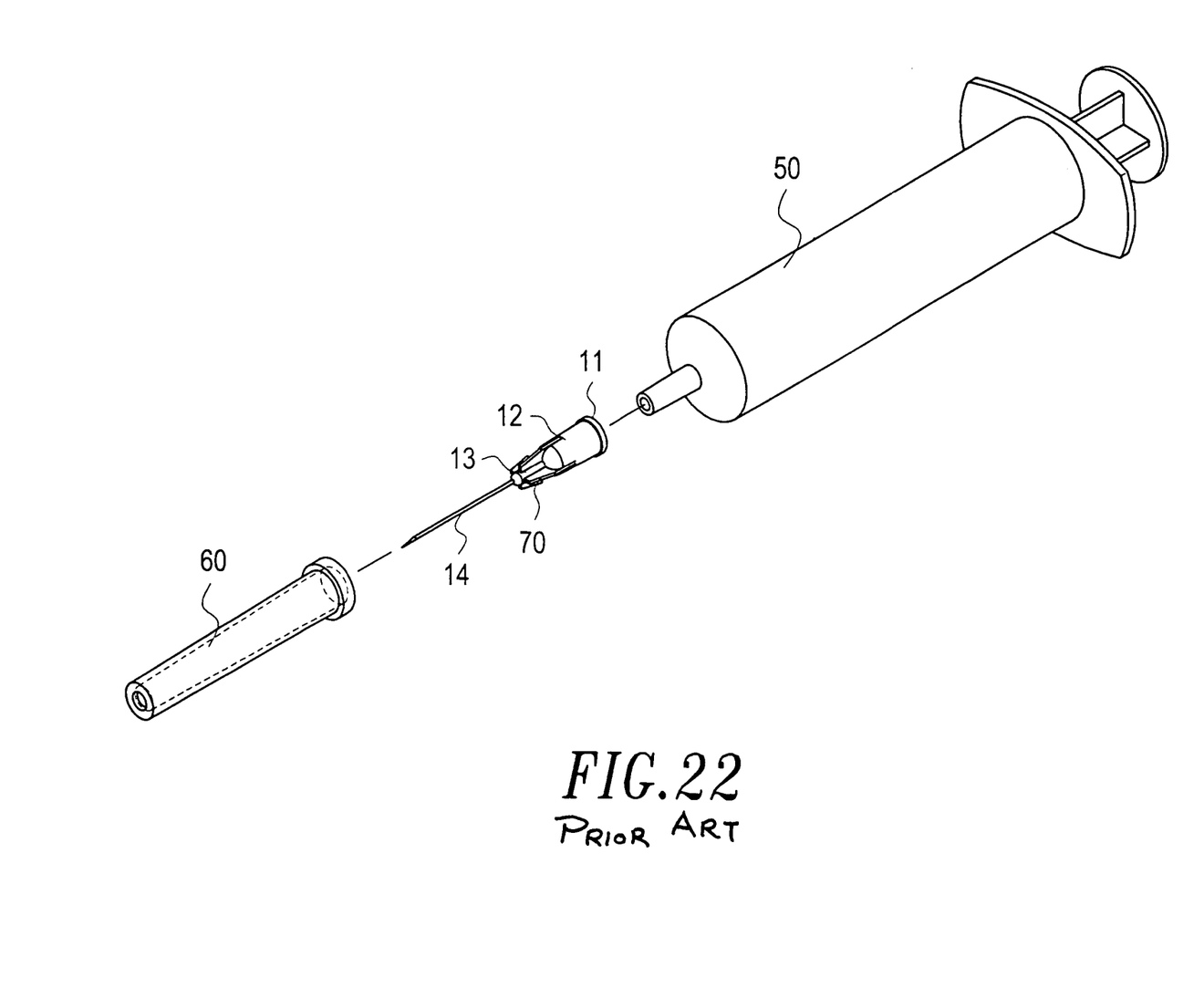
FIG. 22 Exploded view of the typical syringe needle.

Please see FIG. 22, the typical syringe needle is attached to an extended cannula 12 on a base frame 11. In the front end of the cannula is an outer edge part 13, into which a needle 14 is inserted, and several holding and support components 15 are designed on a periphery of the trocar part. The holding and support components 15 extend along a side of cannula 12. In addition, a trocar-setting part is designed inside the syringe needle. The trocar-setting part may be put on the front end of a needle cylinder 50, and the tip of the needle 14 is covered with a needle cover 60. An external wall surface of the needle cover may have the holding and support components 15 inserted therein. The needle cover 60 of a typical syringe needle has to be taken off before drawing or injecting, and then the needle 14 is stabbed into a patient to perform drawing or injecting with the needle cylinder 50. Once finished with the syringe, it may be discarded after putting back on the needle cover 60. However, the needle cover 60 of typical syringe needle is very easy lost, because it has to be removed when performing drawing or injection. Therefore, the needle 14 may lead to risk of exposure when the syringe is discarded. On the other hand, the medical car personnel may be stabbed by needle 14 is the cover is carelessly connected after an injection.

From this we see that many defects still exist in the typical item above, which actually is not a perfect design and should be improved urgently.

In view of the disadvantages derived from the typical syringe needle above, the inventor of this project made improvements and innovations, that eventually resulted in this syringe needle through years of research and concentration.

SUMMARY OF THE INVENTION

This invention focuses on a type of syringe needle that integrates the syringe needle with needle cylinder cover.

One of the purposes of this invention is to provide a type of syringe needle, which avoids the potential risk due to loosing the needle cover.

The elements of a syringe needle for realizing the purpose of this invention include:

A needle head attached to an extended cannula on the base, and a trocar part is designed on the front end of the cannular, into which is a syringe needle inserted;

An external bushing set between the needle and base;

A base with an opening in an appropriate position of the base, which runs through the base and a hole of the trepan boring. A baffle is located inside a perforation. Additionally, on the backside of the base is a connection module.

A barrier structure located between the syringe needle and base. A connection component is located in a front end of this structure incorporated with the connection components of the base.

BRIEF DESCRIPTION OF THE DRAWINGS

The drawings disclose an illustrative embodiment of the present invention, which serves to exemplify the various advantages and objects hereof, and are as follows.

DETAILED DESCRIPTION OF THE PREFERRED EMBODIMENTS

Please see FIGS. 1, 2, 3, and 4, the syringe needle in this invention includes a needle head 1, attached to a base frame 11 with an extended cannula 12. A front end of the cannula has an outer edge 13, into which is inserted a needle 14. In addition, an inside of the needle head 1 has trocar-setting part 15, which connects to the internal conduit of needle 14 at a first end, and at a second end after running through the back end of the base part 11 connects to the needle cylinder 50 or a humoral bag.

An external bushing 2 made from a kind of thin soft material and located between the needle head 1 and a base 3;

The base 3 includes a trocar-admitting part 31 running through a back end of base 3 and a trocar boring 32 connected to the trocar-admitting part 31. There is a hole 33 located on a pre-determined place, which runs through the base 3 and the trocar boring, and a baffle 34 with an opening 341 insertable into the hole 33. Besides, there is a tie-in component 35 on a periphery of the back end of the base 3;

A barrier structure 4 located between the needle head 1 and base 3 and covering the outer fringe of the external bushing 2. In a front of the barrier structure 4 is a connection component 41 that connects with the tie-in component 35 of base 3, and a back end of barrier structure 4 is located against the needle head 1 and base frame 11.

When using the syringe needle, first of all the trocar-setting part 15 should be put on the needle cylinder 50, please see FIGS. 5, 6, 7, 8, 9 and 10. The barrier structure 4 of syringe needle should be pivoted with the tie-in component 35 as the pivotal center, to remove the barrier structure 4 from the base frame 11 of needle head 1. The next step is to push the base 3 toward the base frame 11 to put the trocar boring 32 of base 3 onto the outer edge 13 of needle head 1. Relying on the friction between the wall surfaces of the trocar boring 32 and the outer edge 13, the base 3 will be fastened ion the needle 1. When pushing the base 3 toward the base frame 11, the pressure will cause the external bushing 2 to be accommodated in the trocar-admitting part 31 of base 3. At the same time, the needle 14 will be exposed for stabbing into the affected part of the patient for drawing or injection.

When the drawing or injection is completed, pull out the needle 14 and apply force on the bottom of the barrier structure 4. The base 3 will be moved by virtue of the force on the barrier structure, so that the trocar boring 32 of the base 3 will separate from the outer edge 13 on the needle head 1 and the base 3 will move back to its original position (or directly pull out the needle head 1 from the base 3). Taking the tie-in component 35 as the pivotal center, pivot the barrier structure 4 to allow its bottom to lean against the base frame 11 of needle 1. Pull the baffle 34 on the base 3 upward to allow the baffle to narrow the trocar boring 32 to prevent the injection needle 14 from running out of the trocar boring 32. Now the syringe needle together with the cylinder could be discarded. It is clear from the above mentioned, this invented syringe needle integrates the typical syringe needle with the needle head cover, so as to avoid the potential risk because of the needle 14 if the needle head cover is lost during use. In addition, several bulging buckles 111 could be set on the outer edge of base frame 11 to correspond with position holes 311 located on the trocar-admitting part 31. When the base 3 is pushed to connect with needle head 1, the lobes 111 and hole 311 will engage one another, to prevent the needle from breaking away from base.

Please see the FIGS. 11, 12, 13 and 14, the base 3 may have elastic cells 6 rather than the hole 33. A first elastic cell 6 in the front of base 3 connects a lid 36, which covers trocar boring 32 of base 3 and substitutes for baffle 34. The barrier structure 4 includes a second elastic cell 6 to connect with base 3. In addition, the baffle 34 may be placed in the front of base 3 and connected with base 3 at hinge point 342. The trocar boring 32 of base 3 is revealed by rotating the baffle 34 at hinge point 342. Then needle 14 is inserted through the trocar boring 32.

Figure 1:
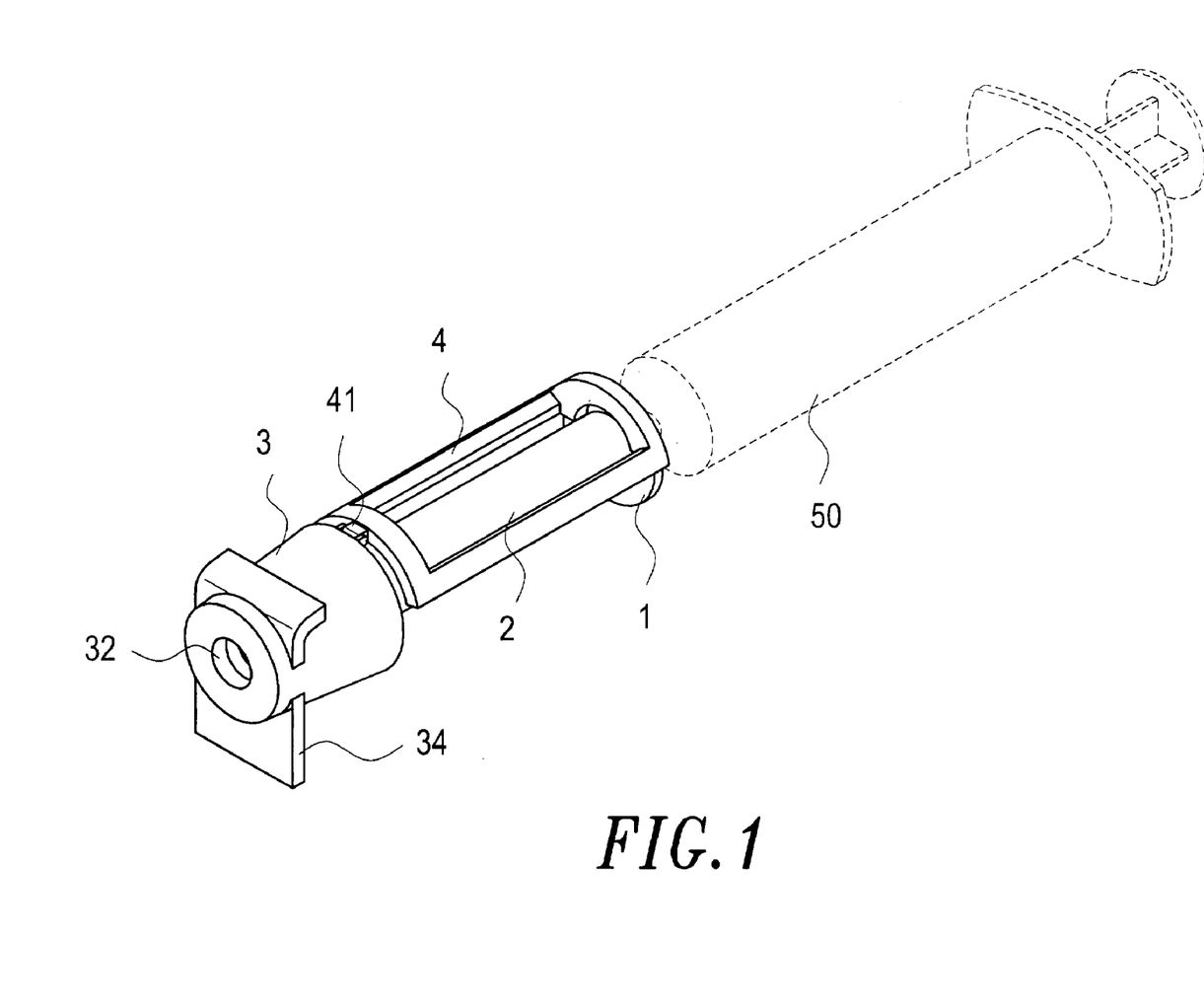
FIG. 1 Three-dimensional outline drawing of the syringe needle.
Figure 2:
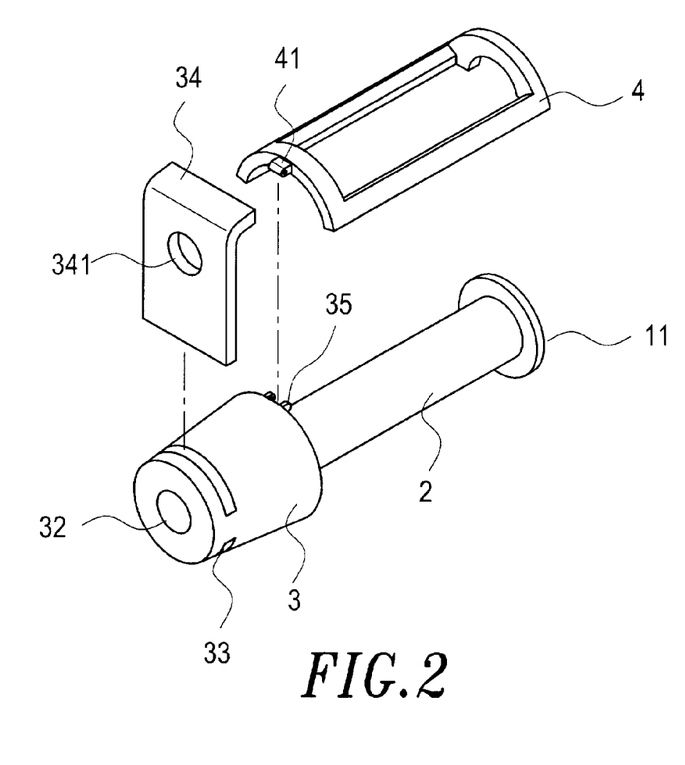
FIG. 2 Three-dimensional exploded view of the syringe needle.
Figure 3:
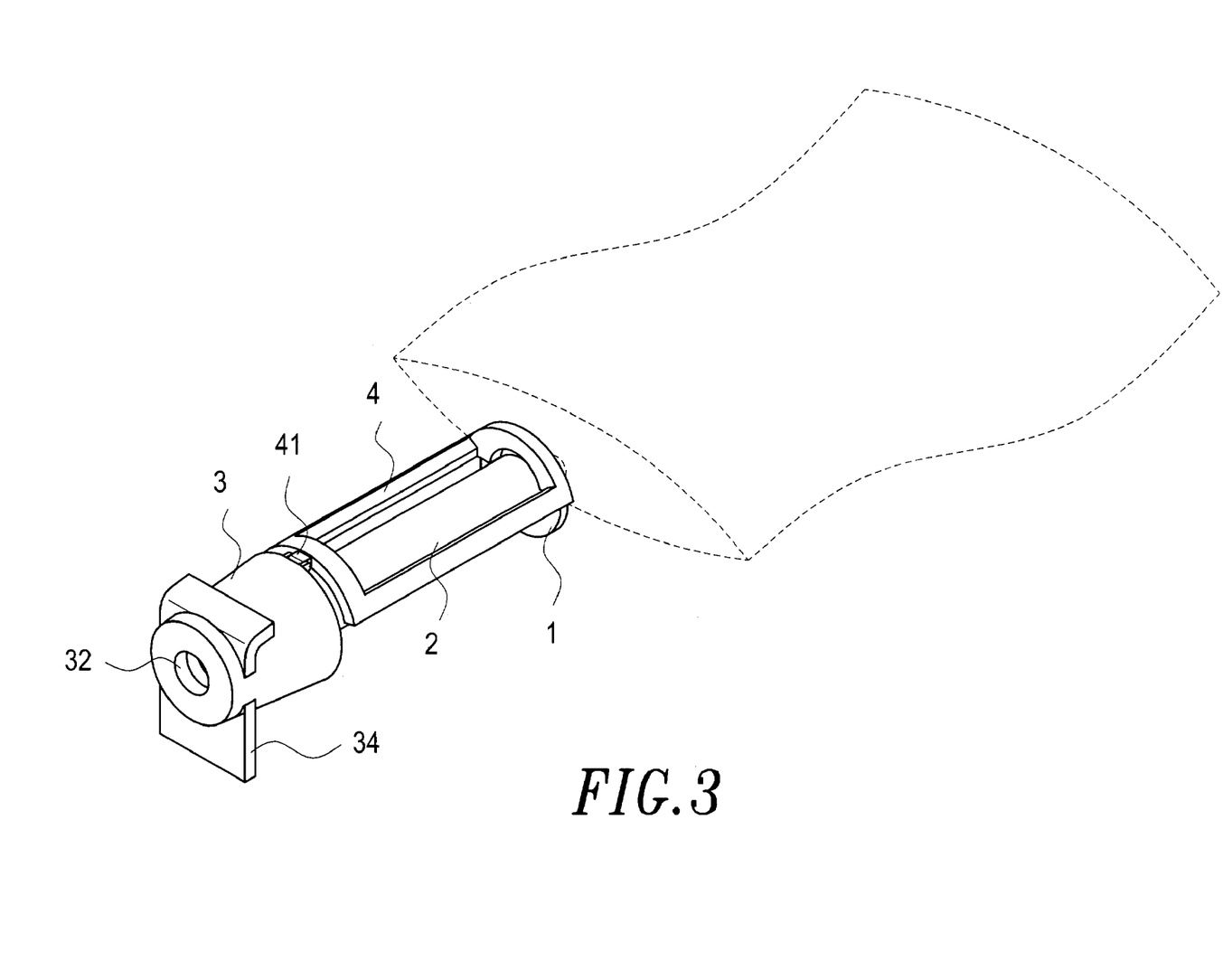
FIG. 3 Usage mode schematic drawing of needle structure.
Figure 4:
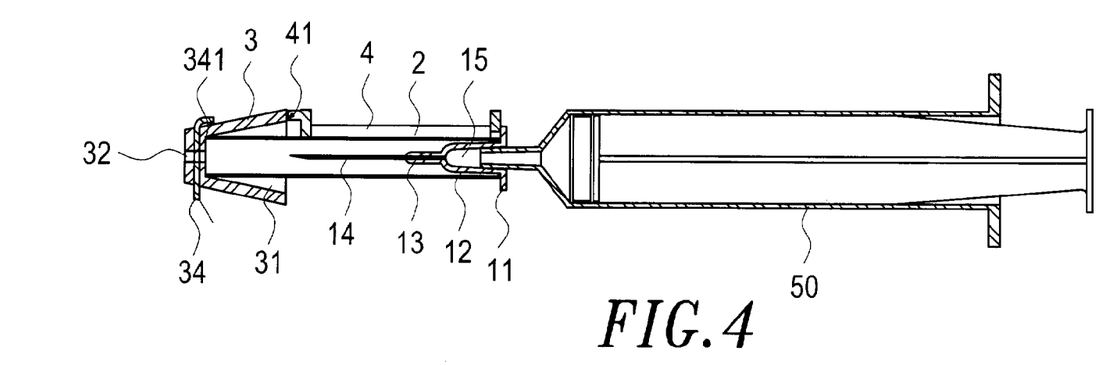
FIG. 4 Side cross-sectional view of the syringe needle.
Figure 5:
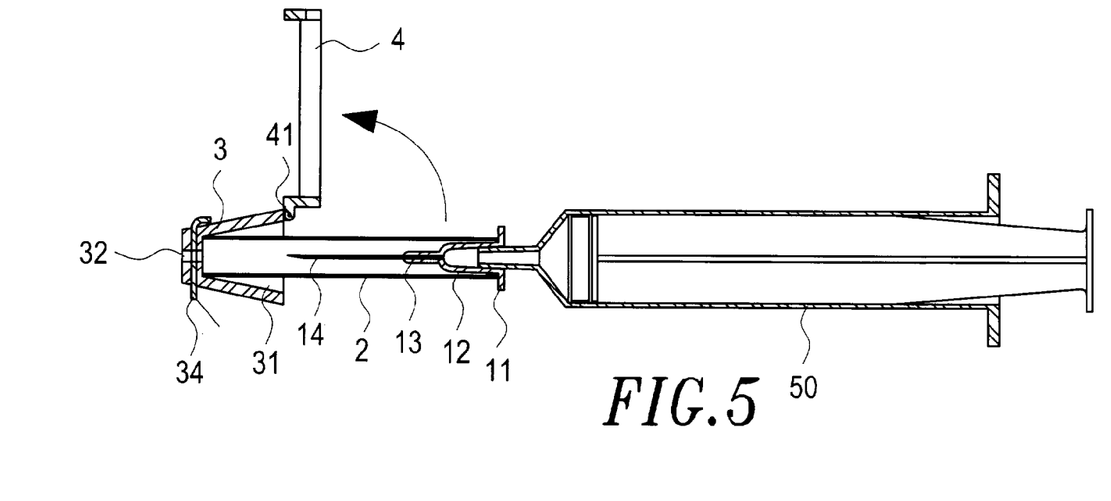
FIG. 5 Side motion schematic drawing (1) of the syringe needle.
Figure 6:
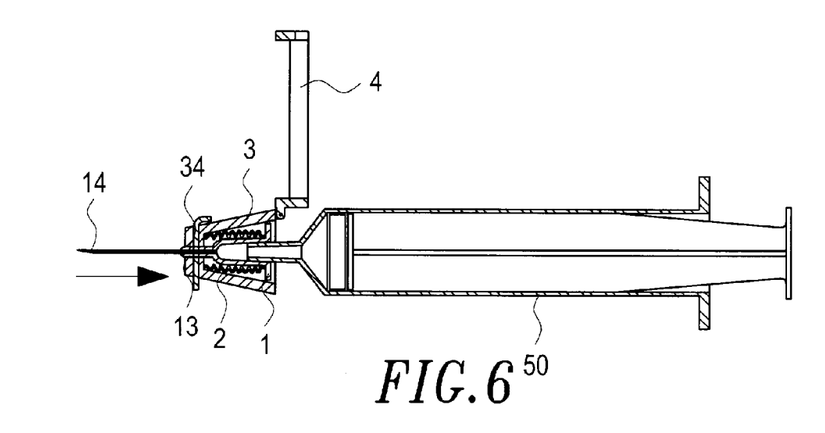
FIG. 6 Side motion schematic drawing (2) of the syringe needle.
Figure 7:
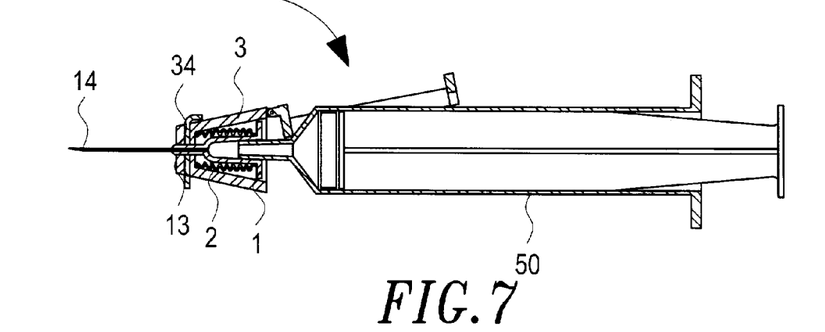
FIG. 7 Side motion schematic drawing (3) of the syringe needle.
Figure 8:
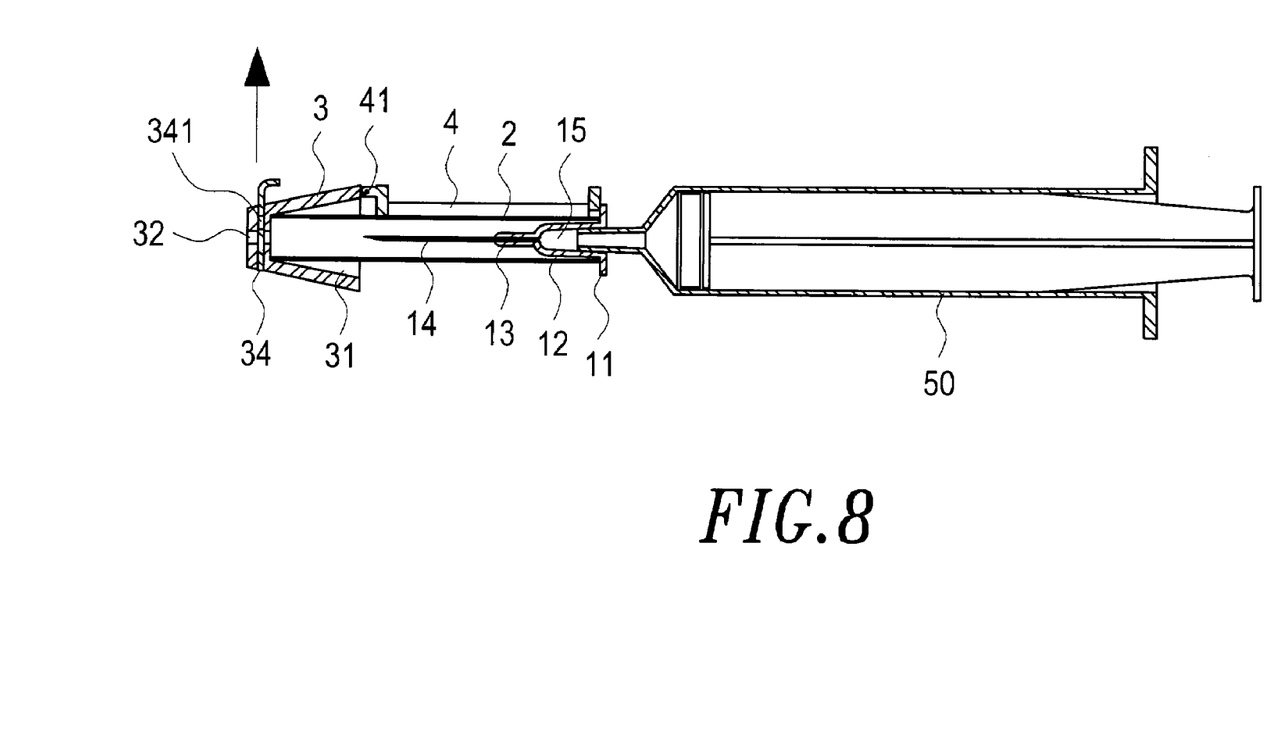
FIG. 8 Side motion schematic drawing (4) of the syringe needle.
Figure 9:
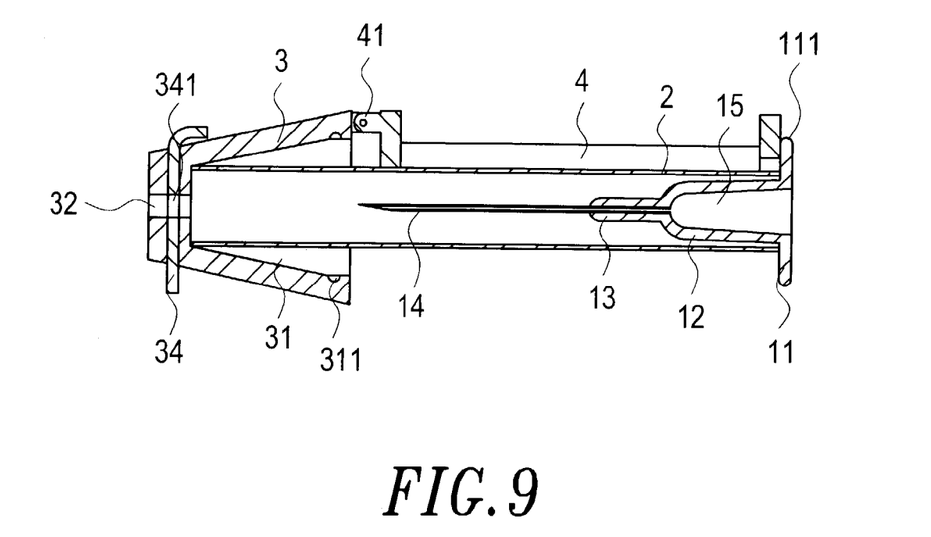
FIG. 9 Side cross-sectional view of the first example of syringe needle.
Figure 10:
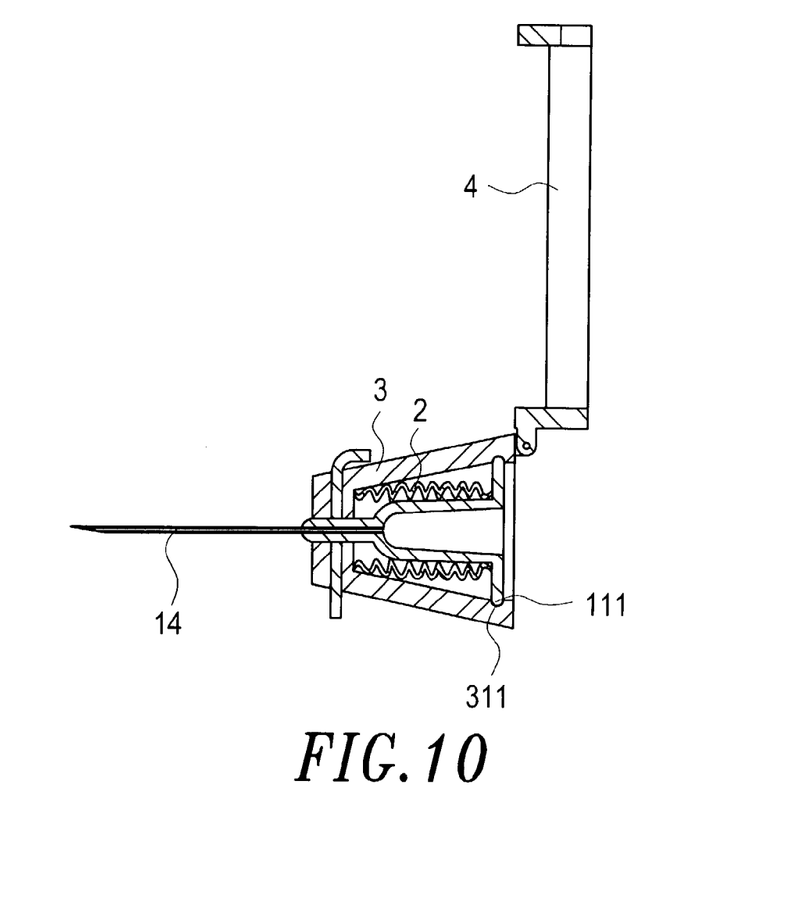
FIG. 10 Side motion schematic drawing of the first example of syringe needle.
Figure 11:
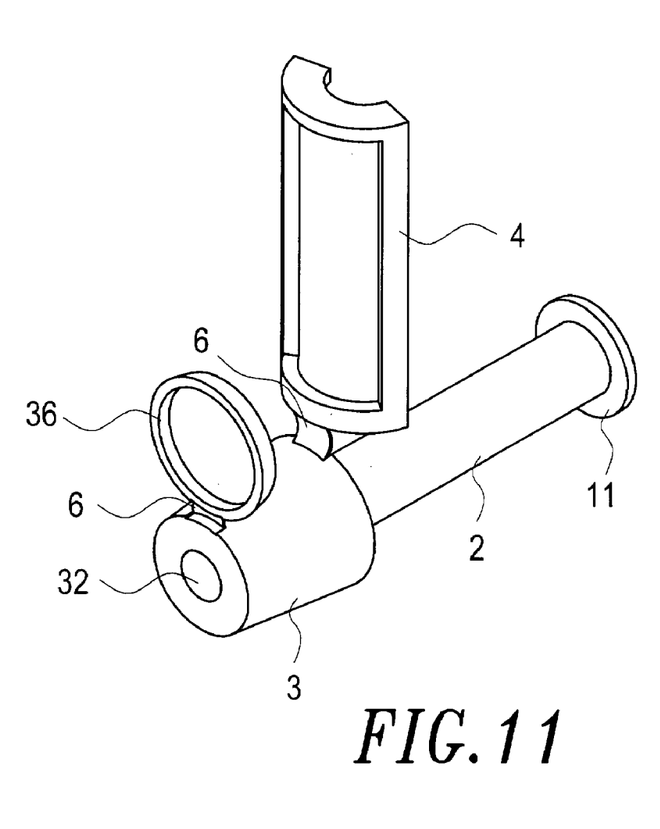
FIG. 11 Three-dimensional view of the second example of syringe needle.
Figure 12:
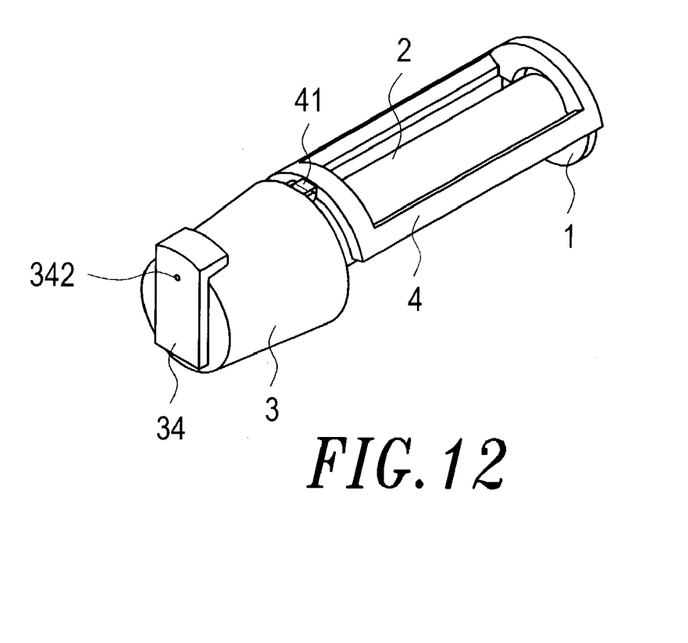
FIG. 12 Three-dimensional outline drawing of the third example of syringe needle.
Figure 13:
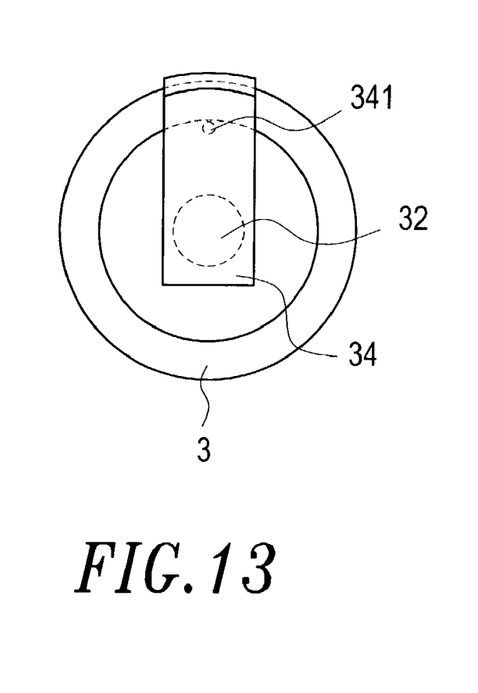
FIG. 13 Front motion schematic drawing (1) of the third example of syringe needle.
Figure 14:
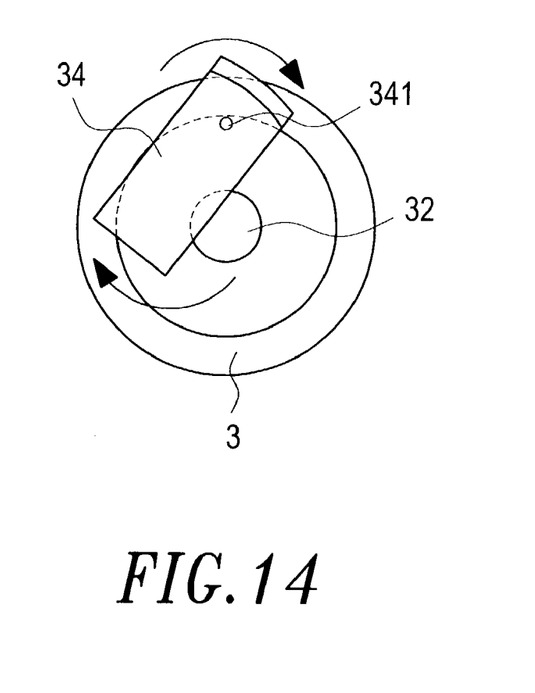
FIG. 14 Front motion schematic drawing (2) of third example of syringe needle.
Figure 15:
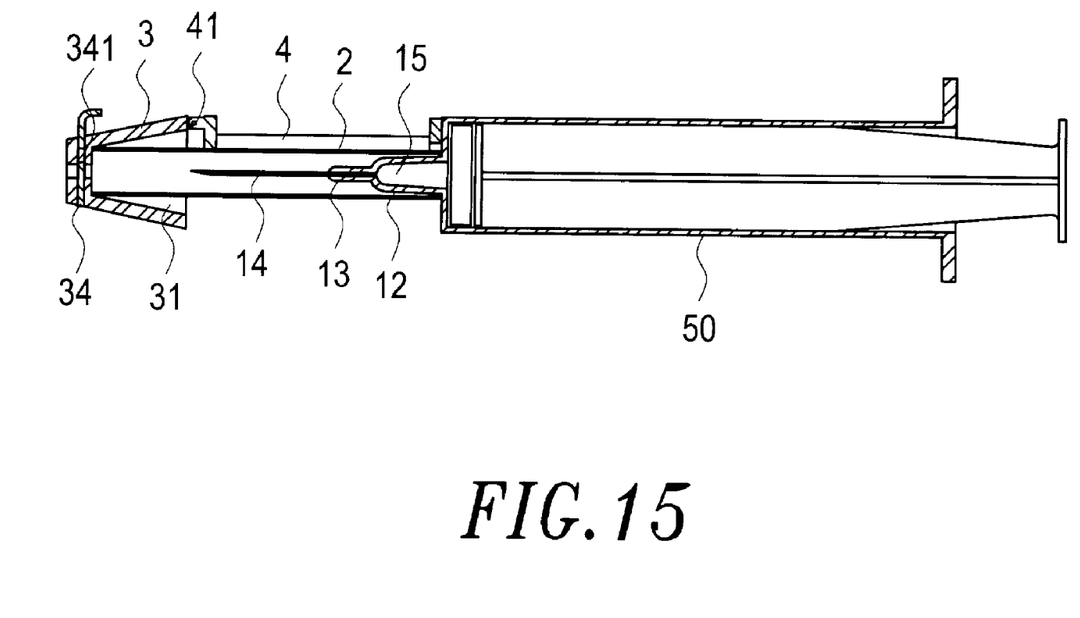
FIG. 15 Side cross-section view of the fourth example of syringe needle.
Figure 16:
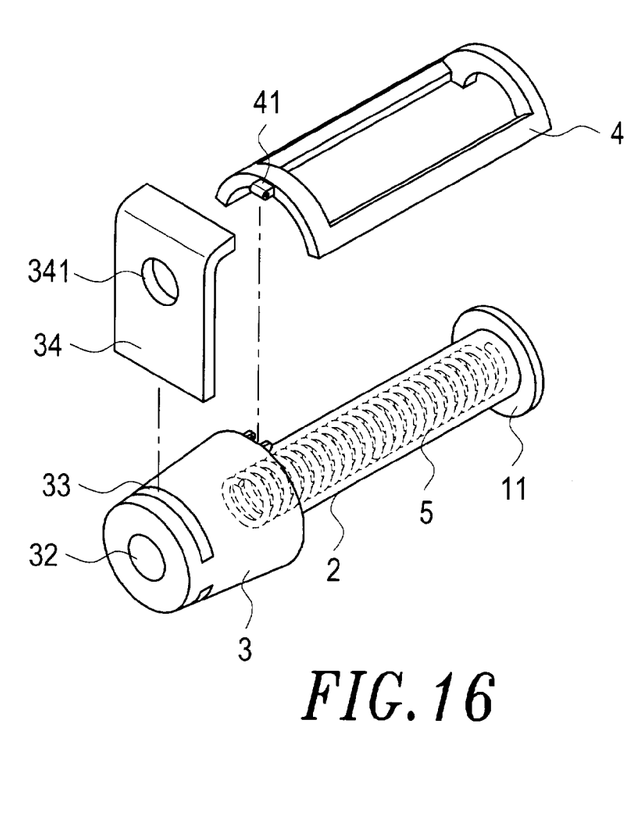
FIG. 16 Three-dimensional outline drawing of fifth example of syringe needle.

Please see FIGS. 15 and 16, in the invention, a spring 5 is placed in the inner edge or outer edge of external bushing 2 of the syringe needle. When the base 3 is separated from needle head 1, the base 3 will be resetted by spring 5. In addition, the syringe needle 14 is integrated with the needle cylinder 50.

Figures 17, 18:
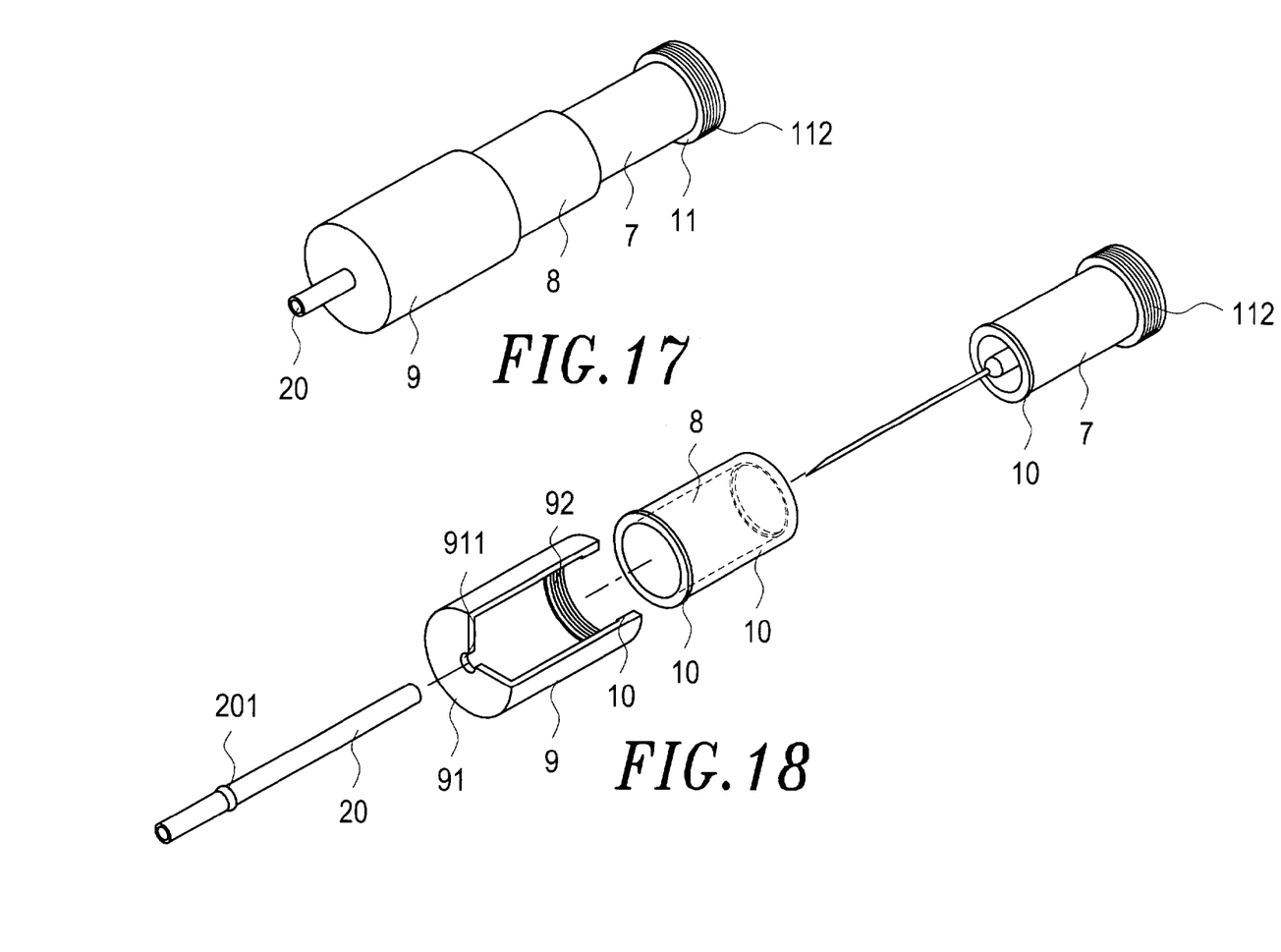
FIG. 17 Three-dimensional outline drawing of sixth example of syringe needle.
FIG. 18 Three-dimensional exploded view of the sixth example of syringe needle.
Figure 19:
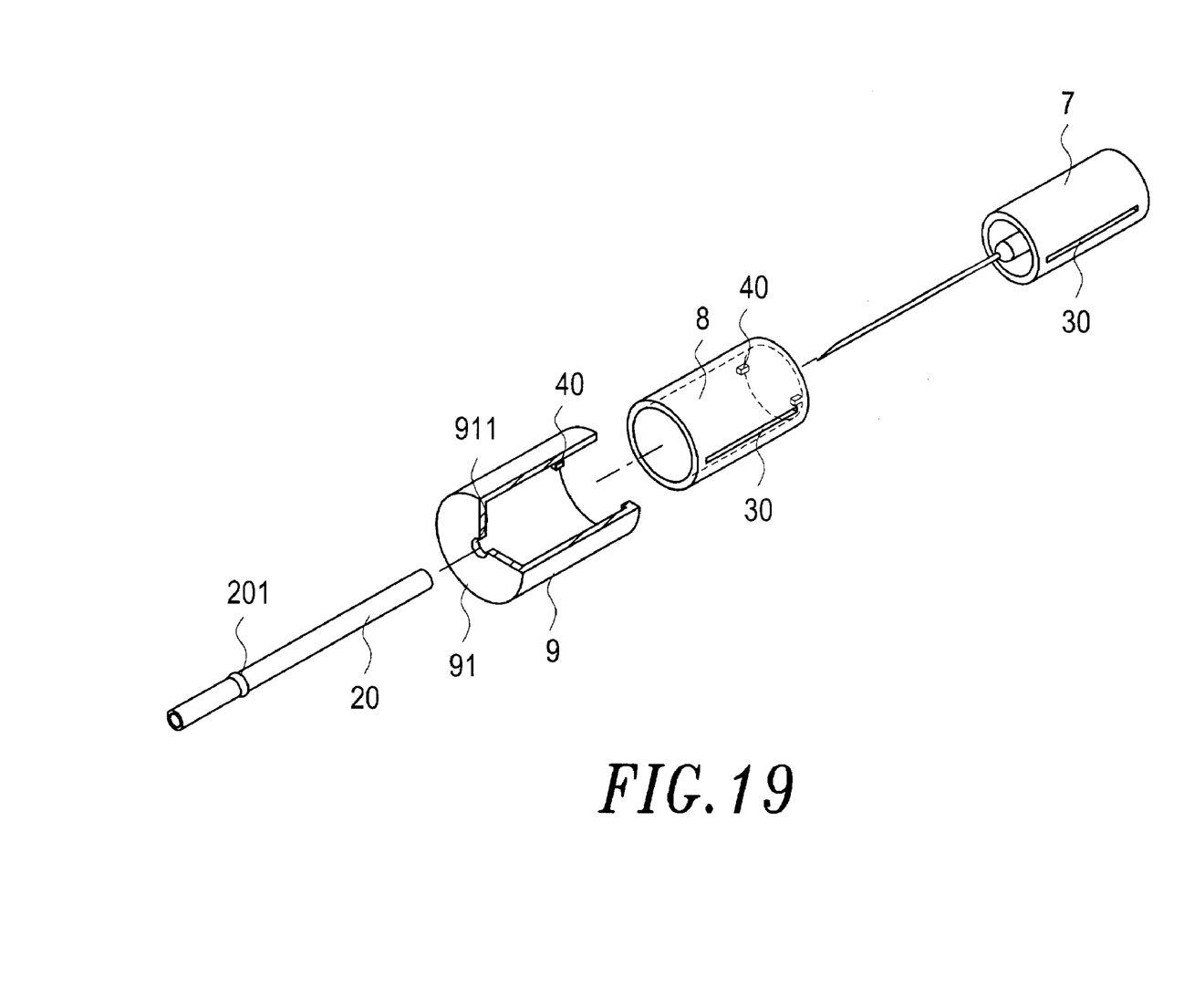
FIG. 19 Three-dimensional exploded view of the seventh example of syringe needle.

Please see FIGS. 17, 18, and 19, in the invention, external bushing 2 and base 3 of the syringe needle will be replaced by an inner edge bushing 7, one or more central bushing 8 and an outer edge bushing 9. The central bushing 8 is positioned around the inner edge bushing 7, and outer edge bushing 9 is positioned around the central bushing 8. A back of the inner edge bushing 7 is connected with base frame 11, and a front outer edge has a protuberance 10. There is a protuberance 10 at both front outer edge and back inner edge of central bushing 8. In addition, outer edge bushing 9 has a protuberance 10 at a back inner edge and a cover plate 91 at a front end. A trocar boring 911 is located through the cover plate 91 and is inserted with a hollow tube 20 having a raised portion 201 connected with an inner wall of cover plate 91. An outer edge of base frame 11 of syringe needle 1 has as screw thread 112. Protuberance 10 of outer edge bushing 9 has a screw thread 92, which will screw with base frame 11. In addition, without protuberance 10 on all bushings, two slide ways 30 are set between the out sides of central bushing 8 and inside of inner edge bushing 7, and two slideways 40 are located between the inner edges of outer edge bushing 9 and the outside of the central bushing 8.

Figure 20:
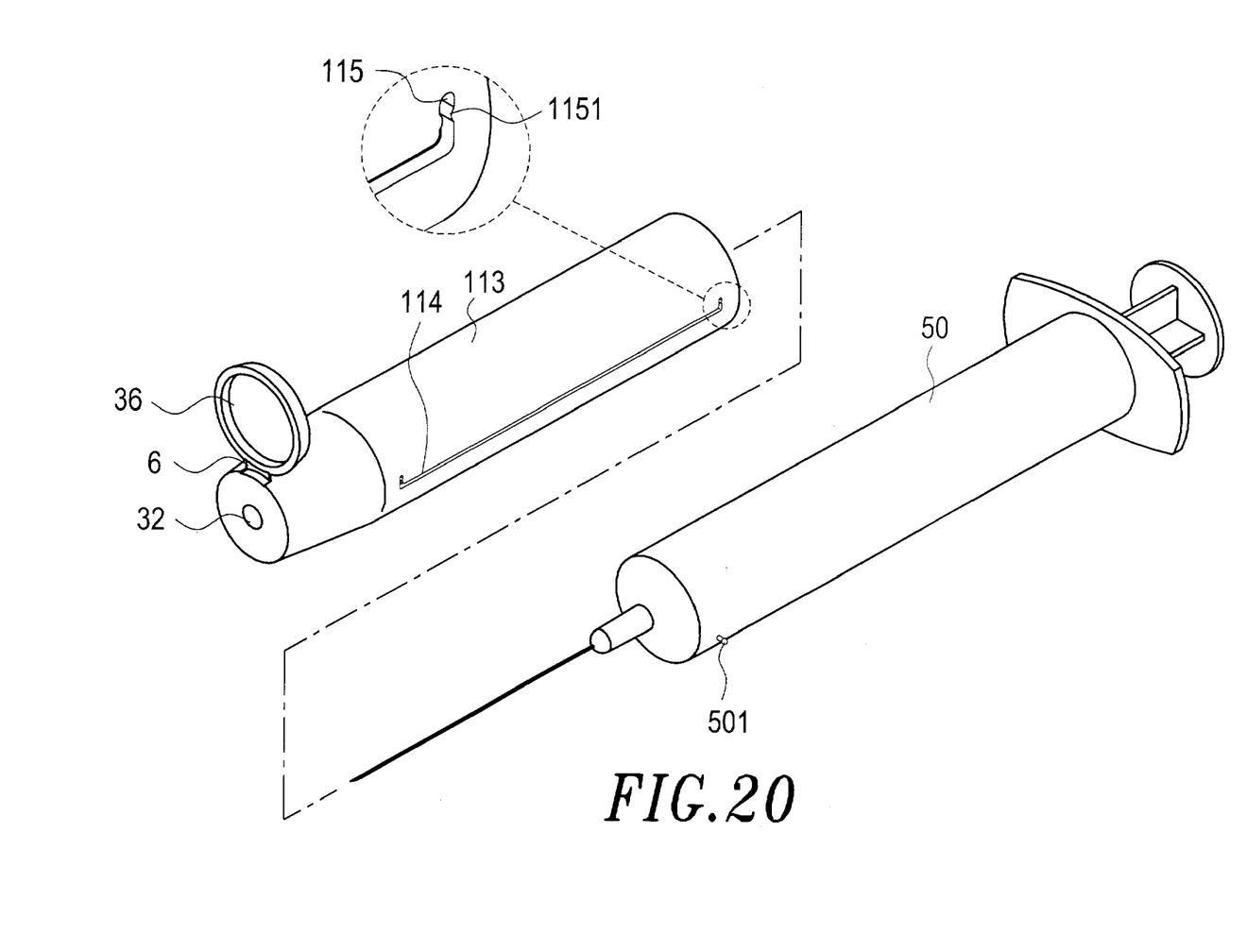
FIG. 20 Three-dimensional exploded view of the eighth example of the needle structure of syringe.
Figure 21:
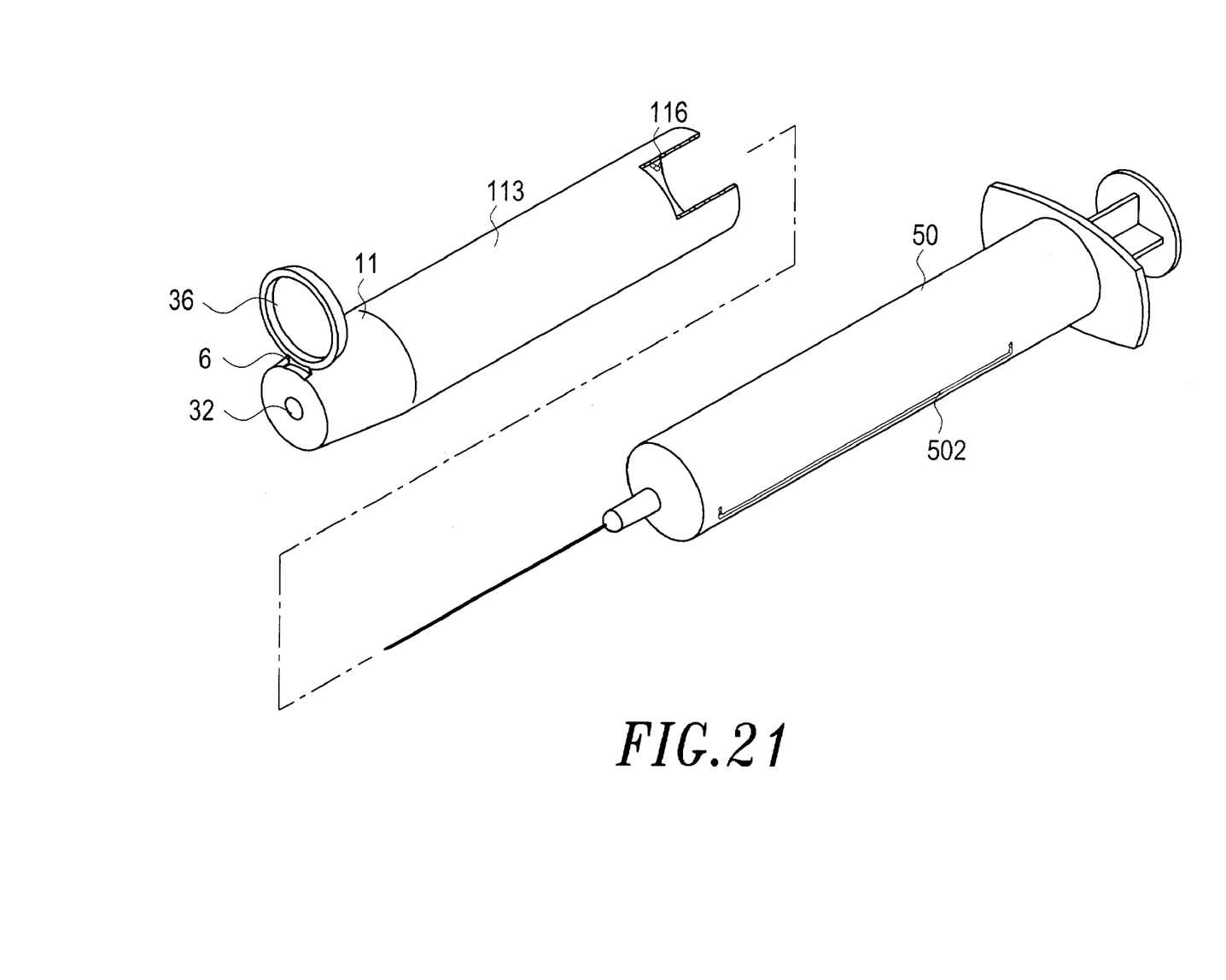
FIG. 21 Three-dimensional exploded view of the ninth example of the needle structure of syringe.

Please see FIG. 20 and FIG. 21, in the present invention, the needle structure of the syringe may integrate with the needle cylinder 50 or the humoral bag. Some fasteners 501 are located on an outer fringe of the needle cylinder 50 near a front end. A sliding part 113 is extended from the back of base 3 of needle head 1, and a runner 114 in the sliding part 113 is installed to contain the fasteners 501 with their locations and number corresponding to the fasteners 501. At each of the two ends of the runner 114 there is a fastener-admitting part 115 with a fastening part 1151. The fastener 501 of the needle cylinder 50 is inserted into each runner 114 and moved such that the syringe needle protrudes out of the fringe of the needle cylinder 50. When the syringe needle slips to the front or the back of the base 3, by turning the syringe needle, the fastener 501 of the needle cylinder 50 is fastened into the fastener-admitting part 115 at the front and back ends of the runner 114. With the fastening part 1151 in the fastener-admitting part 115, the fastener 501 is fixed in the fastener-admitting part 115, and the needle head of the syringe is fixed at the front or back end of the base 3. Moreover, some runners 502 may be located on the outer fringe of the needle cylinder 50. At each of the two sides of the runner 502, there is a trocar-admitting part, which protrudes two fastening parts respectively at its two inner side. In the sliding part 113 of the syringe needle near to the back end, some fasteners 116 is located, the locations and number correspond with that of the runner 502 of needle cylinder 50. With integration of the fastener 116 of the syringe needle and type runner 502 of the needle cylinder 50, the needle of the syringe can be extended out of the fringe of the needle cylinder 50.

Compared with the above quotative cases and other typical technologies, the syringe needle in the invention has the following benefits:

1. An external busing connects with a base, and the backside of base connects with barrier structure, which closely contacts with the head of the syringe needle, so that the head of syringe needle will be used with the combination of the cover.

2. The combination of the head and the cover of syringe needle will prevent the risks resulting in the exposure to the syringe needle by loosing the cover when rejecting and withdrawing.

3. This invention combines the head of syringe needle with the cover to prevent the risks during the operation by medical care personnel.

Many changes and modifications in the above described embodiment of the invention will, of course, be carried out without departing from the scope thereof. Accordingly, to promote the progress in science and the useful arts, the invention is disclosed and is intended to be limited only by the scope of the appended claims.

What is claimed is:

1. A syringe needle, comprising:
   a) a needle head attached to an extended cannula and a needle inserted through a front outer edge of the extended cannula;
   b) a trocar-setting part in the extended cannula is connected at a first end to the inner conduit of the needle and at a second end to one of a needle cylinder and a fluid delivery system;
   c) an external bushing made of a soft material placed between the extended cannula and a base;
   d) the base having a trocar-admitting part located in a back of the base, a trocar boring on a front end of the base connected with the trocar-admitting part, a hole running through the base and the trocar boring, the hole has a baffle with an opening, and a connecting part on a backside of the base; and
   e) a barrier structure located between the extended cannula and the a connecting part of the base and removably covering the external bushing, a connecting component connecting a front of the barrier structure to the base and a back end of the barrier structure is removably connected with the needle head.

2. The syringe needle according to claim 1 wherein a spring is located in an interior of the external bushing.

3. The syringe needle according to claim 1 wherein the external bushing is made of plastic, rubber or other soft material.

4. The syringe needle according to claim 1 wherein the needle is integrally formed with one of the needle cylinder and the humoral bag.

* * * * *